(12) United States Patent
Sartorelli et al.

(10) Patent No.: US 9,169,194 B2
(45) Date of Patent: Oct. 27, 2015

(54) METERING RING

(71) Applicants: Lorenza Sartorelli, Ober-Ramstadt (DE); Andreas Perl, Bobenheim-Roxheim (DE); Udo Gropp, Bad Endorf (DE); Arndt Selbach, Erftstadt (DE); Stefanie Sohnemann, Overath (DE); Matthias Groemping, Pfungstadt (DE); Norbert Mnich, Erlensee (DE); Thomas Mertz, Bensheim (DE)

(72) Inventors: Lorenza Sartorelli, Ober-Ramstadt (DE); Andreas Perl, Bobenheim-Roxheim (DE); Udo Gropp, Bad Endorf (DE); Arndt Selbach, Erftstadt (DE); Stefanie Sohnemann, Overath (DE); Matthias Groemping, Pfungstadt (DE); Norbert Mnich, Erlensee (DE); Thomas Mertz, Bensheim (DE)

(73) Assignee: EVONIK RÖHM GmbH, Darmstadt (DE)

(*) Notice: Subject to any disclaimer, the term of this patent is extended or adjusted under 35 U.S.C. 154(b) by 41 days.

(21) Appl. No.: 13/838,525

(22) Filed: Mar. 15, 2013

(65) Prior Publication Data

US 2013/0211140 A1  Aug. 15, 2013

Related U.S. Application Data

(62) Division of application No. 13/256,638, filed as application No. PCT/EP2010/053962 on Mar. 26, 2010, now abandoned.

(30) Foreign Application Priority Data

Apr. 23, 2009 (DE) .................. 10 2009 002 592

(51) Int. Cl.
*C07C 231/06* (2006.01)
*B01J 4/00* (2006.01)
*B01J 4/02* (2006.01)

(52) U.S. Cl.
CPC .............. *C07C 231/06* (2013.01); *B01J 4/002* (2013.01); *B01J 4/02* (2013.01); *B01J 2204/002* (2013.01); *Y10T 137/8158* (2015.04)

(58) Field of Classification Search
CPC ........... C07C 231/06; B01J 4/00; B01J 4/001; B01J 4/008
See application file for complete search history.

(56) References Cited

U.S. PATENT DOCUMENTS

| 2,548,759 | A | 4/1951 | Allen |
| 3,540,853 | A * | 11/1970 | Kulling et al. ............... 422/158 |
| 5,295,397 | A | 3/1994 | Hall et al. |
| 5,461,932 | A | 10/1995 | Hall et al. |
| 5,935,490 | A | 8/1999 | Archbold et al. |
| 6,234,168 | B1 | 5/2001 | Bruna |
| 6,969,490 | B2 * | 11/2005 | Marx et al. .................... 422/110 |
| 7,461,618 | B2 | 12/2008 | Pors et al. |
| 2003/0152500 | A1 | 8/2003 | Dalziel et al. |
| 2004/0187770 | A1 | 9/2004 | Calabrese et al. |
| 2005/0202095 | A1 | 9/2005 | Daiziel et al. |
| 2006/0111586 | A1 * | 5/2006 | Schladenhauffen et al. . 564/123 |
| 2006/0231149 | A1 | 10/2006 | Kulkarni |
| 2008/0011250 | A1 | 1/2008 | Pors et al. |

FOREIGN PATENT DOCUMENTS

| DE | 101 44 681 | | 3/2003 |
| DE | 101 44 681 A1 | | 3/2003 |
| DE | 10 2004 055425 | | 5/2006 |
| DE | 10 2004 055 425 B4 | | 6/2007 |
| JP | 63-23734 | | 2/1988 |
| JP | 2000-213681 A | | 8/2000 |
| JP | 2000-213681 A | * | 8/2000 |
| JP | 2002-213681 A | | 8/2000 |
| JP | 2005-506174 A | | 3/2005 |
| JP | 2007-521131 A | | 8/2007 |
| JP | 2008-520529 A | | 6/2008 |
| SU | 209416 A1 | | 1/1968 |
| WO | WO 2006/113883 A2 | | 10/2006 |

OTHER PUBLICATIONS

Office Action issued Jan. 27, 2014 in Japanese Patent Application No. 2012-506425 (submitting English translation only).
Combined Taiwanese Office Action and Search Report issued May 23, 2014 in Patent Application No. 099112336 (with English language translation.
Russian Decision concerning the granting of a patent for an invention issued Jul. 14, 2014 in Patent Application No. 2011147120/05 (070629) with English language translation.
Chinese Office Action and Search Report issued Aug. 16, 2013 in Chinese Patent Application No. 201080016396.9 (with English-language translation).
International Search Report issued May 27, 2010 in PCT/EP10/053962 filed Mar. 26, 2010.
Combined Written Opinion and Search Report issued Sep. 12, 2013 in Singapore Patent Application No. 201107772-4.
Internal Reconsideration Report issued Mar. 18, 2015 in Japanese Patent Application No. 2012-506425 (submitting English translation only).

* cited by examiner

*Primary Examiner* — Paul A Zucker

(74) *Attorney, Agent, or Firm* — Oblon, McClelland, Maier & Neustadt, L.L.P.

(57) ABSTRACT

The present invention relates to an apparatus for metering flowable media or gases, and to the use thereof.

17 Claims, 3 Drawing Sheets

Graph A: Yield comparison with and without metering ring

METERING RING

This is a divisional application of U.S. application Ser. No. 13/256,618, filed Sep. 15, 2011, which is a 371 of PCT/EP2010/053962 filed on Mar. 26, 2010.

BACKGROUND OF THE INVENTION

1. Field of the Invention

Metering of free-flowing media or gases, and the use thereof.

2. Description of the Background (Meth)acrylic acid and (meth)acrylic esters are important products in the chemical industry, which serve as starting materials for many important products. A maximum yield and a particularly high purity coupled with low preparation costs are therefore essential for the economic success of a preparation process for such an important product. Even relatively small improvements with regard to the yields, the service lives of the plants or similar process features lead to a significant advance with regard to the amount of undesired by-products and the preparation costs.

The methacrylamide used to prepare methacrylic acid can preferably be obtained by what is known as the ACH process. Proceeding from hydrogen cyanide and acetone, acetone cyanohydrin is prepared in a first step, and is then converted to methacrylamide. These steps are described, inter alia, in U.S. Pat. No. 7,253,307, EP-A-1 666 451 and PCT/EP2007 059092.

Acetone cyanohydrin is prepared by commonly known processes (see, for example, Ullmanns Enzyklopädie der technischen Chemie, 4$^{th}$ Edition, Volume 7). Frequently, the reactants used are acetone and hydrogen cyanide. The reaction is an exothermic reaction. In order to counteract decomposition of the acetone cyanohydrin formed in this reaction, the heat of reaction is typically removed by a suitable apparatus. The reaction can in principle be conducted as a batchwise process or as a continuous process; when a continuous method is preferred, the reaction is frequently performed in a loop reactor configured correspondingly.

The acetone cyanohydrin prepared by different known preparation processes is typically subjected to a distillative workup. This involves freeing the stabilized crude acetone cyanohydrin of low-boiling constituents by means of an appropriate column. A suitable distillation process can, for example, be conducted using only one column. However, it is likewise possible in the case of a corresponding purification of crude acetone cyanohydrin to use a combination of two or more distillation columns, also in combination with a falling-film evaporator. It is additionally possible to combine two or more falling-film evaporators or else two or more distillation columns with one another.

The crude acetone cyanohydrin is generally transferred from the storage to the distillation with a temperature of about 0 to about 15° C., for example a temperature of about 5 to about 10° C. In principle, the crude acetone cyanohydrin can be introduced directly into the column. However, it has been found to be useful in some cases when the crude cool acetone cyanohydrin first absorbs, by means of a heat exchanger, some of the heat from the product already purified by distillation. Therefore, in a further embodiment of the process described here, the crude acetone cyanohydrin is heated by means of a heat exchanger to a temperature of about 60 to 80° C.

The distillative purification of the acetone cyanohydrin is effected by means of a distillation column having more than 5 and preferably more than 10 trays, or by means of a cascade of two or more correspondingly suitable distillation columns. The column bottom is preferably heated with steam. It has been found to be advantageous when the bottom temperature does not exceed a temperature of 140° C.; it has been possible to achieve good yields and good purification when the bottom temperature is not greater than about 130° C. or not higher than about 110° C. The temperature figures are based on the wall temperature of the column bottom.

The crude acetone cyanohydrin is supplied to the column body in the upper third of the column. The distillation is preferably performed under reduced pressure, for example at a pressure of about 50 to about 900 mbar, especially of about 50 to about 250 mbar, and with good results between 50 and about 150 mbar.

At the top of the column, gaseous impurities, especially acetone and hydrogen cyanide, are withdrawn, and the gaseous substances removed are cooled by means of a heat exchanger or a cascade of two or more heat exchangers. In this context, preference is given to using brine cooling with a temperature of about 0 to about 10° C. This gives the gaseous constituents of the vapours the opportunity to condense. The first condensation stage can take place, for example, at standard pressure. It is, however, likewise possible, and has in some cases been found to be advantageous, when this first condensation stage is effected under reduced pressure, preferably at the pressure which exists in the distillation. The condensate is passed on into a cooled collecting vessel and collected there at a temperature of about 0 to about 15° C., especially at about 5 to about 10° C.

The gaseous compounds which do not condense in the first condensation step are removed from the reduced pressure space by means of a vacuum pump. It is possible in principle to use any vacuum pump. However, it has been found to be advantageous in many cases when a vacuum pump which, owing to its design, does not lead to the introduction of liquid impurities into the gas stream is used. Preference is therefore given here to using, for example, dry-running vacuum pumps.

The gas stream which escapes on the pressure side of the pump is conducted through a further heat exchanger which is preferably cooled with brine at a temperature of about 0 to about 15° C. This condenses constituents which are likewise collected in the collecting vessel which collects the condensates already obtained under vacuum conditions. The condensation performed on the pressure side of the vacuum pump can be effected, for example, by means of one heat exchanger, but also with a cascade of two or more heat exchangers arranged in series in parallel. Gaseous substances remaining after this condensation step are removed and sent to any further utilization, for example a thermal utilization.

The condensates collected can likewise be utilized further in any way. However, it has been found to be extremely advantageous from an economic point of view to recycle the condensates into the reaction for preparation of acetone cyanohydrin. This is preferably done at one or more points which enable access to the loop reactor. The condensates may in principle have any composition provided that they do not disrupt the preparation of the acetone cyanohydrin. In many cases, the predominant amount of the condensate will, however, consist of acetone and hydrogen cyanide, for example in a molar ratio of about 2:1 to about 1:2, frequently in a ratio of about 1:1.

The acetone cyanohydrin obtained from the bottom of the distillation column is first cooled in a first heat exchanger by the cold crude acetone cyanohydrin supplied to a temperature of about 40 to about 80° C. Subsequently, the acetone cyanohydrin is cooled by means of at least one further heat exchanger to a temperature of about 30 to about 35° C. and optionally stored intermediately.

In a further process element, acetone cyanohydrin is subjected to a hydrolysis. At various temperature levels, and after a series of reactions, this forms methacrylamide as the product.

The conversion is accomplished in a manner known per se to the person skilled in the art by reaction between concentrated sulphuric acid and acetone cyanohydrin. The reaction is exothermic, and so heat of reaction can be removed from the system in an advantageous manner.

Here too, the conversion can again be performed in a batchwise process or in continuous processes. The latter has been found to be advantageous in many cases. When the reaction is performed in the course of a continuous process, the use of loop reactors has been found to be useful. Loop reactors are known in the technical field. These may be configured, for example, in the form of tubular reactors with recycling. The reaction can be effected, for example, in only one loop reactor. However, it may be advantageous when the reaction is performed in a cascade of two or more loop reactors.

A suitable loop reactor in the context of the process described has one or more feed sites for acetone cyanohydrin, one or more feed sites for concentrated sulphuric acid, one or more gas separators, one or more heat exchangers and one or more mixers. The loop reactor may comprise further constituents, such as conveying means, pumps, control elements, etc.

As already described, the hydrolysis of acetone cyanohydrin with sulphuric acid is exothermic. In parallel to the main reaction, several side reactions take place, which lead to lowering of the yield. In the preferred temperature range, the decomposition of acetone cyanohydrin, likewise an exothermic and rapid reaction, plays a significant role. The heat of reaction which arises in the course of the reaction, however, has to be at least substantially removed from the system, since the yield falls with increasing operating temperature and rising residence time. It is possible in principle to achieve rapid and comprehensive removal of the heat of reaction with corresponding heat exchangers. However, it may also be disadvantageous to cool the mixture too greatly before the metered addition of acetone cyanohydrin, since high turbulence is needed both for mixing and for efficient heat removal. Since the viscosity of the mixture being stirred rises significantly with falling temperature, the flow turbulence falls correspondingly, in some cases down to the laminar range, which leads in the heat exchanger to less efficient heat removal, and to slower and less homogeneous mixing when the acetone cyanohydrin is metered in.

What is required is rapid mixing of acetone cyanohydrin and reaction mixture, since the acetone cyanohydrin should react before it decomposes owing to the heating. Fine dropletization of the reactant, which means a large specific interface area, causes a preference for the desired reaction at the droplet surface over the heating of the droplet volume with subsequent decomposition. A fine distribution of acetone cyanohydrin has been found to be advantageous, since the reaction takes place at the droplet surface.

Furthermore, excessively low temperatures in the reaction mixture can lead to crystallization of constituents of the reaction mixture on the heat exchangers. This further worsens the heat transfer, which causes a significant decline in yield. Furthermore, the loop reactor cannot be charged with the optimal amounts of reactants, and so the efficiency of the process suffers overall.

SUMMARY OF THE INVENTION

It is therefore an object of the invention to improve the supply and the fine distribution of free-flowing media or gases in pipelines or tubular reactors, and ideally also to improve mixing operations.

This object is achieved by an apparatus for metering free-flowing media or gases, characterized in that one or more metering rings with metering sites [11] provided in pipelines, tubular reactors or loop reactors are used.

It has been found that, surprisingly, the supply and fine distribution, enabled with the metering ring, of a free-flowing medium or gas over the entire tube circumference or the cross-sectional tube area results in a significant improvement of the mixing operation. Large amounts can be mixed over a short distance.

DETAILED DESCRIPTION OF THE INVENTION

Figure 1:
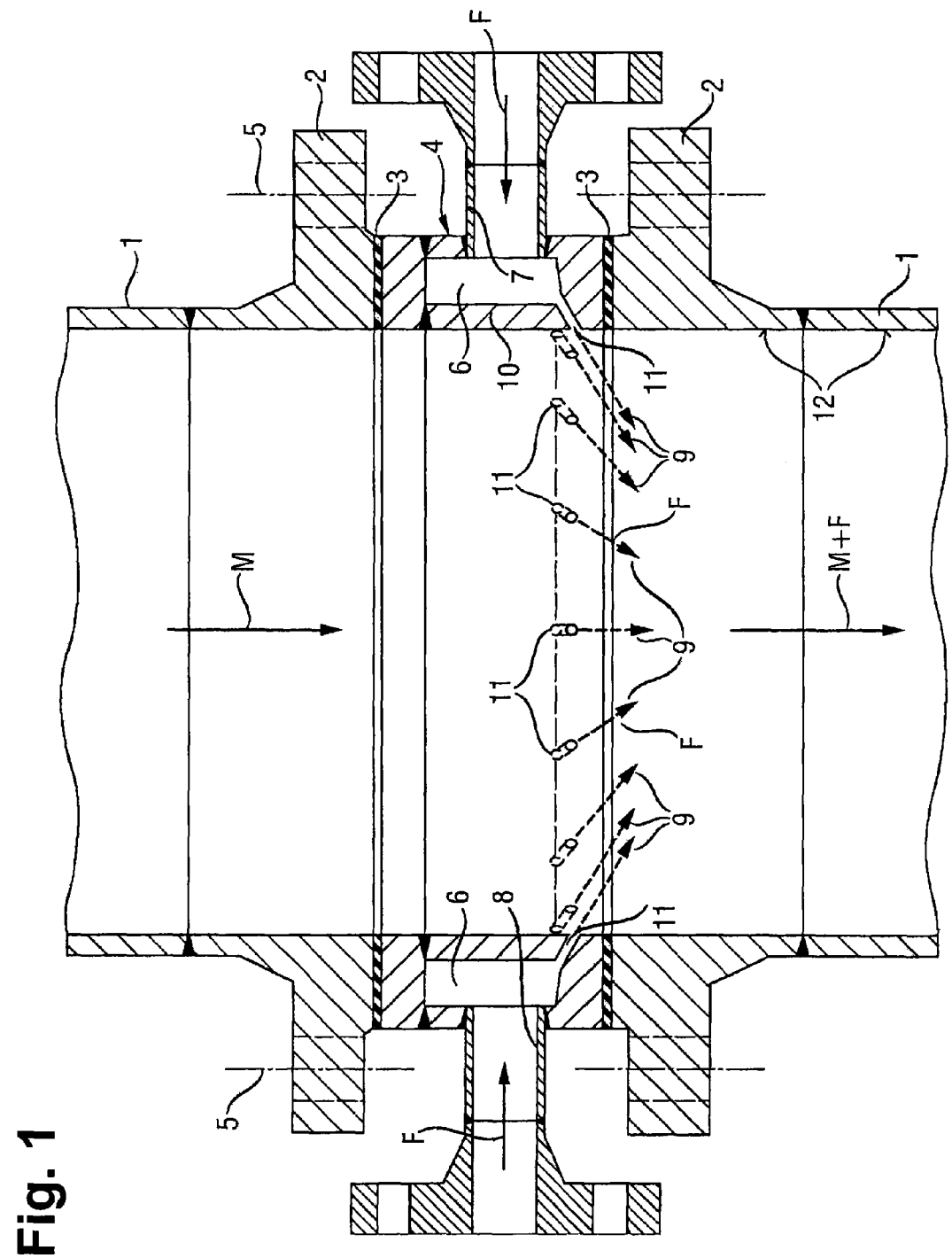
FIG. 1
Longitudinal section through a pipeline section with installed metering ring
FIG. 2
Enlarged partial diagram of a modified embodiment
FIG. 3
A graph comparing yields using a metering ring versus a static mixer.

The inventive metering ring may have various embodiments. For instance, many small metering sites [11] may be incorporated into the ring, or few large metering sites (FIG. 1). The metering sites may also project through tubes [13] into the interior of the tube (FIG. 2), and in particular embodiments also tubes of different lengths.

The metering ring may be cooled or heated according to the metering task.

Here lies a further advantage of the inventive external ring which is not heated by the surrounding medium, for example a metering lance inserted into the tube. In addition, this ring could be used to cool the acetone cyanohydrin, which would be much more complicated in construction terms, for example, in a metering lance.

A particular embodiment is a metering ring in which the metered addition is effected under elevated pressure.

The apparatus may assume any suitable three-dimensional shape, and is preferably constructed in the form of a ring. It is also possible here to use double or multiple rings.

The metering ring is particularly suitable for use in continuous processes. The metering ring is preferably used in the continuous preparation of methacrylamide by hydrolysis of acetone cyanohydrin with sulphuric acid. One example of another field of use would be the preparation of acetone cyanohydrin from acetone and hydrogen cyanide.

According to the invention, the reaction is effected continuously in a tubular reactor or loop reactor. The terms "continuously" and "tubular reactor" are known in the technical field. A continuous reaction is understood to mean especially reactions in which reactants are added to and products are removed from the reaction mixture over a prolonged period. Tubular reactors comprise at least one tubular region in which the reaction can proceed. These reactors typically have a relatively simple construction, and so the capital costs are comparatively low.

The reactants can be introduced into the tubular reactor by means of a pump. To prevent maintenance-related operation shutdowns, it is also possible to provide two or more pumps which can be connected in parallel. Viewed in flow direction, the reactants can appropriately be mixed with a metering ring upstream of the pumps, i.e. on the pump suction side, and the system more preferably does not have any further internals for mixing in the region between the pumps and the tubular reactor. The metering ring may, however, also be part of the pump and may be integrated into the pump housing. These measures can achieve surprising advantages with regard to operational reliability and the service lives of the plant, and in relation to the yield and the purity of the product.

The components of the plant which come into contact with corrosive substances, especially the tubular reactor, the pumps and the phase separators, are built from suitable materials, for example an acid-resistant metal, for example zirconium, tantalum, titanium or stainless steel, or a coated metal which has, for example, an enamel layer or a zirconium layer. It is additionally also possible to use polymers, for example PTFE-coated components, graphitized components or graphite parts, especially in pumps.

In one configuration of the process, part of the volume flow of a stream of acetone cyanohydrin, preferably about two thirds to about three quarters, is introduced into a first loop reactor. A first loop reactor preferably has one or more heat exchangers, one or more pumps, one or more mixing elements and one or more gas separators. The circulation flows which pass through the first loop reactor are preferably in the range from about 50 to 650 m$^3$/h, more preferably in a range from 100 to 500 m$^3$/h and additionally preferably in a range from about 150 to 450 m$^3$/h. In at least one further loop reactor which follows downstream of the first loop reactor, the circulation flows are preferably in a range from about 40 to 650 m$^3$/h, more preferably in a range from 50 to 500 m$^3$/h and additionally preferably in a range from about 60 to 350 m$^3$/h. Moreover, a preferred temperature difference over the heat exchanger is about 1 to 20° C., particular preference being given to about 2 to 7° C.

The supply of the acetone cyanohydrin, according to the invention via a metering ring, can in principle be effected anywhere in the loop reactor. However, it has been found to be advantageous when the supply is effected into a mixing element, for example into a mixer with moving parts or a static mixer, or at a well-mixed site. The sulphuric acid is advantageously supplied upstream of the acetone cyanohydrin addition. Otherwise, however, it is likewise possible to introduce the sulphuric acid into the loop reactor anywhere.

The inventive metering ring is used to feed in the medium, for example the sulphuric acid or the acetone cyanohydrin, just upstream of or in a pump. Thus, the highly turbulent flow in the pump housing is utilized to mix the reactants, thus utilizing a conveying machine simultaneously as a mixing machine. The mixing capacity of the pump is therefore exploited in an advantageous manner.

The ratio of the reactants in the loop reactor is controlled such that a sulphuric acid excess is present. The excess of sulphuric acid is, based on the molar ratio of the constituents, about 1.8:1 to about 3:1 in the first loop reactor, and about 1.1:1 to about 2:1 in the last loop reactor.

In some cases, it has been found to be advantageous to conduct the reaction in the loop reactor with such an excess of sulphuric acid. The sulphuric acid here may serve, for example, as a solvent and keep the viscosity of the reaction mixture low, which can ensure more rapid removal of heat of reaction and a lower temperature of the reaction mixture. This can bring significant yield advantages. The temperature in the reaction mixture is about 85 to about 150° C.

The removal of heat is ensured by one or more heat exchangers in the loop reactor. It has been found to be advantageous when the heat exchangers possess a suitable sensor system for adjusting the cooling output, in order to prevent excessive cooling of the reaction mixture for the reasons mentioned above. For example, it may be advantageous to measure the heat transfer at certain points or continuously in the heat exchanger or in the heat exchangers, and adjust the cooling output of the heat exchangers thereto. This can be done, for example, via the coolant itself. It is also equally possible to achieve corresponding heating of the reaction mixture through corresponding variation in the addition of the reactants and through the generation of more heat of reaction. A combination of both possibilities is also conceivable. The loop reactor preferably additionally possesses at least one gas separator. The gas separator can be used firstly to withdraw product formed continuously from the loop reactor. Secondly, gases formed in the course of the reaction can thus be withdrawn from the reaction space. The gas formed is principally carbon monoxide. The product withdrawn from the loop reactor is preferably transferred into a second loop reactor. In this second loop reactor, the reaction mixture comprising sulphuric acid and methacrylamide as obtained by the reaction in the first loop reactor is reacted with the remaining substream of acetone cyanohydrin. In the course of this, the excess of sulphuric acid from the first loop reactor, or at least a portion of the excess sulphuric acid, reacts with the acetone cyanohydrin to form further sulphoxyisobutyramide (SIBA). The performance of the reaction in two or more loop reactors has the advantage that, owing to the sulphuric acid excess in the first loop reactor, the pumpability of the reaction mixture and hence the heat transfer and ultimately the yield are improved. Again, at least one mixing element, at least one heat exchanger and at least one gas separator are arranged within the second loop reactor. The reaction temperature in the second loop reactor is likewise about 90 to about 120° C.

The problem of pumpability of the reaction mixture, of heat transfer and of a very low reaction temperature applies as much in every further loop reactor as it does in the first. Therefore, the second loop reactor too advantageously possesses a heat exchanger, the cooling output of which can be regulated by means of a corresponding sensor system.

Again, the acetone cyanohydrin is supplied in a suitable mixing element, preferably in a static mixer or the inventive metering ring. The product can be withdrawn from the gas separator of the second loop reactor, and it can be heated to a temperature of about 130 to about 180° C. to complete the conversion and to form the methacrylamide.

The heating is preferably performed in such a way that the maximum temperature is attained only for a very short period, for example for a period of about one minute to about 30 minutes, especially for a period of about two to about eight minutes or about three to about five minutes. This can in principle be effected in any desired apparatus for achieving such a temperature for such a short period. For example, the energy can be supplied in a conventional way by means of electrical energy or by means of steam. However, it is equally possible to supply the energy by means of electromagnetic radiation, for example by means of microwaves.

It has been found to be advantageous in various cases when the heating step is effected in a heat exchanger with a two-stage or multistage arrangement of tube coils which may preferably be present in an at least double, opposing arrangement. The reaction mixture is heated rapidly to a temperature of about 130 to 180° C.

The amide solution thus obtainable generally has a temperature of more than 100° C., typically a temperature of about 130 to 180° C. Cooling to temperatures less than 130° C. is likewise possible.

In addition to the use of the inventive apparatus in chemical processes, there are many further possible uses.

For example, the metering ring can also be used in overland pipelines for mineral oil transport. Flow improvers have to be added to the crude oil at regular intervals. At these feed sites, the flow improver is usually added through a nozzle. The large volume flow forces the medium metered in primarily to the inside of the tube, and the conversion proceeds poorly and only over a long distance. With the inventive metering ring, it is possible to ensure that the flow improver is added to the crude oil over the entire tube cross section.

A similar application is in the additions of chemicals needed in oil and gas extraction.

The invention further provides for the use of the inventive metering device in chemical processes, preferably in processes in which rapid mixing and fine distribution of a medium are required. Ideally, at the point of metered addition, the medium supplied is reacted or mixed completely with the medium flowing past. In the case of metered addition, for example, of one drop of liquid, until fine mixing with the other medium, a minimum distance should be covered to the mixing point.

It has been found that the inventive metering ring enables almost ideal mixing or conversion in the case of supply or free-flowing media or gases at one feed site.

Compared to the conventional metering apparatus which have one metering site, more homogeneous distribution over the tube cross section is effected in the case of the inventive metering apparatus via one ring with a plurality of metering sites. This significantly improves the mixing result and simultaneously shortens the mixing time. The inner wall of the metering ring is permeated by any number of injection channels. Preferably 2 to 20 and more preferably 16 injection channels arranged homogeneously over the circumference are used. These may, individually or in common, be tilted with respect to the inner wall of the pipeline at an angle of 1° to 179°, preferably of 20° to 120°, more preferably of 60°. In the case of the known metering apparatus with one metering site, strong flows within the tube have the result that the medium metered in is forced to the tube wall by the medium flowing past, and hence only poor mixing, if any, takes place. These metering sites therefore cannot be used simultaneously for mixing. Downstream of the metering sites, mixing operations additionally have to be initiated. This is done by the incorporation of static mixing elements or the incorporation of pumps or the like.

The known methods of metered addition along a tube with a plurality of metering sites are unsuitable for many chemical processes, since the chemical conversion is adversely affected over the long mixing distance. The long mixing distance results in thermal decomposition, and the yield is thus worsened.

It is possible to dispense with the use of static mixing elements which, in the case of use of corrosive media, additionally have to be exchanged regularly and hence lead to shutdown times. The use of static mixing elements always also leads to undesired pressure drops.

It is particularly advantageous to install the metering ring upstream of a pump. Ideally, the metering ring is positioned directly upstream of the suction stub of the circulation pump. It is thus possible to utilize the turbulences in the pump for mixing.

It is equally possible to use the metering ring in the centrifugal pump, ideally close to the point at which the kinetic energy is at its greatest, in order to bring about ideal mixing. Metered addition in the middle of the pump leads to the effect that the distance from the pump outlet is long and hence the mixing distance is also long.

In special cases, it is possible to dispense with a mixer of a pump through the use of the metering ring.

For example, the supply of a gas, optionally of an inert gas, can generate turbulence in the medium which flows through the tube. It is thus possible to prevent sedimentation of a suspension by laminar flow within the tube.

A broad and homogeneous distribution over the entire cross section of a tube can be achieved by virtue of the metering sites or tubes of the metering ring being of different lengths. It is thus possible to meter the reactant into the tube interior in a controlled manner.

The inventive metering apparatus has a broad spectrum of application, wherever rapid and/or homogeneous metered addition of free-flowing media or gases is required. It is possible to meter in liquids with low or high viscosity, but also suspensions, emulsions, gases, etc. It is used in chemical systems such as pipelines or tubular reactors. The metering ring serves as a metering apparatus and/or mixer.

In a particularly preferred application, the metering ring is used in the hydrolysis of acetone cyanohydrin with sulphuric acid to give methacrylamide.

The invention is illustrated in detail by the drawings which follow:

LIST OF REFERENCE NUMERALS

1 Pipeline
2 Pipe flange
3 Seals
4 Metering ring
5 Clamping means
6 Distributor chamber of 4
7 Feed stub for fluid F
8 Feed stub for fluid F
9 Injection
10 Inner wall of metering ring 4
11 Injection channels (metering sites)
12 Inner wall of 1
13 Tubes
14 Stop collar for 13
15 Exit edge on 13
16 Metering point
d Diameter of injection channel 11
D External diameter of tube 13
α Angle
Y Radial projection of 13,15
M Medium
F Fluid The drawings show two working examples of the inventive metering ring.

According to FIG. 1, the inventive metering ring 4 is mounted by means of clamping means 5 shown schematically in a pipeline 1 through which a medium M flows, between two tube flanges 2 and two seals 3.

The metering ring 4 has a peripheral distributor chamber 6 which is supplied with the fluid F to be metered by two feed stubs 7 and 8.

The inner wall 10 of the metering ring 4 is permeated by preferably sixteen injection channels 11 distributed homogeneously over the circumference. These are, again preferably, inclined at an angle α of 60° with respect to the inner wall 12 of the pipeline 1.

This ensures homogeneous injection 9 of the fluid F into the flow of the medium M.

Figure 2:
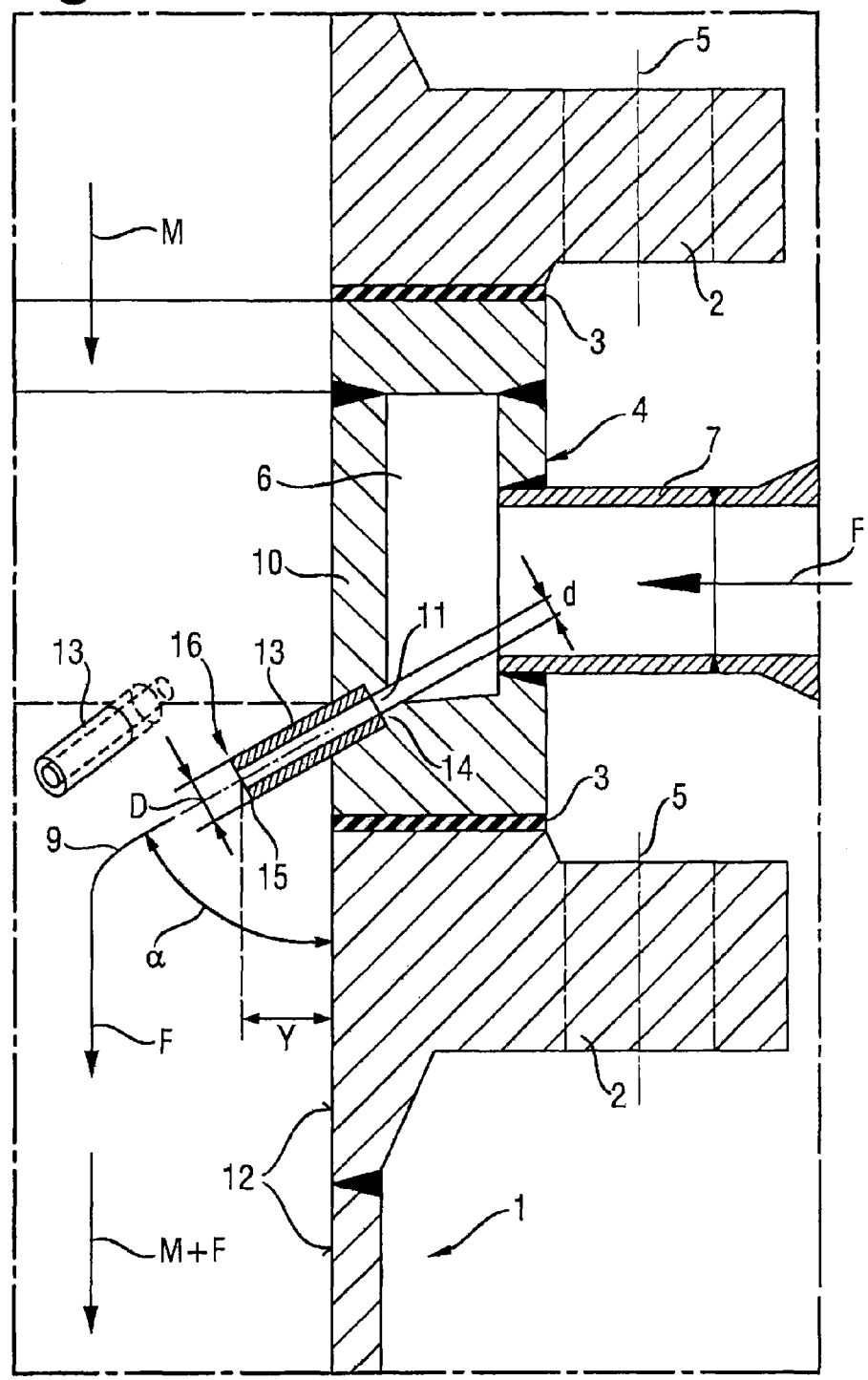

The solution according to FIG. 2 envisages inserting into the injection channels 11 tubes 13 which have a radial projection Y with respect to the inner wall 12 of the pipeline 1.

In this case, the end of the tube 13, which thus extends somewhat into the flow of the medium M, constitutes the metering point 16.

This optimizes the introduction of the fluid F into the flow of medium M, in such a way that the fluid F cannot run along the inner wall 12 of the pipeline 1, and the droplet is torn off only in the media flow as such at the metering point 16, owing to the flow of medium M around the exit edges 15 of the tube 13.

In order that the tubes 13 cannot be pressed into the distributor chamber 6, a stop collar 14 is provided, which is formed by the diameter difference between the diameter d of the injection channel 11 and the outer diameter D of the tube 13.

This construction feature results in rational mounting of the metering tubes 13, while simultaneously ensuring the predetermined position of the radial distance Y of the metering point 16 from the inner wall 12 of the pipeline 1.

The examples given hereinafter are given for better illustration of the present invention, but are not capable of restricting the invention to the features disclosed herein.

EXAMPLES

In several operating tests, yield determinations were carried out. This experiment determined the effect of the metering ring.

The yield was determined in a process regime with metering ring and a downstream pump as a dynamic mixer, compared to the static mixer used conventionally. The pump is arranged immediately after (connected downstream of) the metering ring in the flow direction. The metering ring is flanged (mounted) directly onto the suction nozzle of the pump, in order to ensure a very short path of the ACH before mixing and thus to achieve very rapid mixing. The pump, in the process regime with the inventive metering ring, is a circulation pump, which is used in a loop reactor typically for circulation of the amide mixture.

Figure 3:
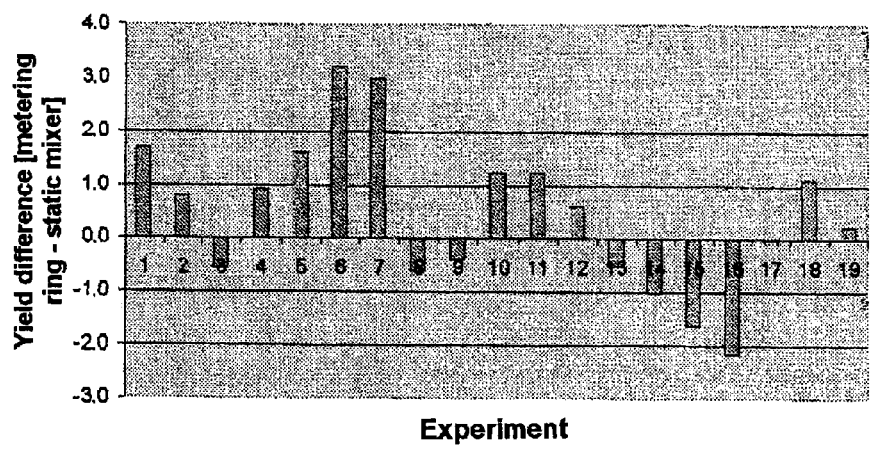

The yields obtained are compared in graph A as shown in FIG. 3. Various test parameters were varied, and the yields were determined by sampling and analyses of the amide mixture.

The majority of the measurements give an increase in yield. Positive yield differences up to 3.2% show an improvement in the yields as a result of the use of the metering ring.

The invention claimed is:

1. A method for carrying out a chemical reaction by continuously feeding reactants in a tubular or loop reactor, comprising metering one of the reactants through one or more metering rings located at one or more metering sites in the tubular or loop reactor, wherein at the point of metered addition, said one of the reactants is rapidly mixed and reacted with remaining reactants, wherein
   the chemical reaction is the preparation of methacrylamide by hydrolysis of acetone cyanohydrin with concentrated sulfuric acid, and
   at least one of the metering rings is not heated by a surrounding medium, has a peripheral distribution chamber, and is installed in a position that is upstream of or in a pump.

2. The method of claim 1, wherein the acetone cyanohydrin is the reactant that is fed through the one or more metering rings.

3. The method of claim 1, wherein the acetone cyanohydrin exits through the one or more metering rings in the form of a fine distribution of droplets.

4. The method of claim 1, wherein the sulfuric acid is the reactant that is fed through the one or more metering rings.

5. The method of claim 1, wherein the temperature of at least one metering ring is controlled.

6. The method of claim 1, wherein metered addition is carried out at elevated pressure.

7. The method of claim 1, wherein at least one of the metering rings has an inner wall that is permeated by a plurality of injection channels.

8. The method of claim 1, wherein at least one of the metering rings enables supply and fine distribution of the reactants over the entire circumference or cross section of the reactor.

9. The method of claim 1, wherein tubes project from the metering sites and exit into the interior of the reactor.

10. The method of claim 9, wherein the tubes are of different length.

11. The method of claim 1, wherein the concentrated sulfuric acid is used in a molar excess to the acetone cyanohydrin, and a reaction mixture comprising concentrated sulfuric acid and methacrylamide is fed from the loop reactor, and acetone cyanohydrin is fed, to another loop reactor.

12. The method of claim 11, wherein the acetone cyanohydrin is fed to the other loop reactor through one or more metering rings of said other loop reactor.

13. The method of claim 1, wherein at least one of the metering rings is in a position that is upstream of a pump.

14. The method of claim 13, wherein the pump is arranged immediately after the at least one of the metering rings in the flow direction.

15. The method of claim 1, wherein the at least one of the metering rings is in a pump and is flanged or mounted directly onto a suction nozzle of the pump.

16. The method of claim 15, wherein the pump is a circulation pump.

17. The method of claim 13, wherein the pump is a circulation pump.

\* \* \* \* \*